(12) United States Patent
Grumann et al.

(10) Patent No.: US 7,309,804 B2
(45) Date of Patent: Dec. 18, 2007

(54) PROCESS FOR PURIFYING 1,2-DICHLOROETHANE

(75) Inventors: Helmut Grumann, Perach (DE); Manfred Stoger, Burgkirchen (DE); Jurgen Eichler, Kastl (DE); Dieter Jaculi, Burgkirchen (DE); Winfried Lork, Erftstadt (DE); Arend Greve, Erftstadt (DE); Jan Wilkens, Erftstadt (DE); Peter Kammerhofer, Burgkirchen (DE); Hermann Tropp, Emmerting (DE)

(73) Assignees: Vinnolit Technologie GmbH & Co., Burgkirchen (DE); Vintron GmbH, Hurth-Knapsack (DE)

( * ) Notice: Subject to any disclaimer, the term of this patent is extended or adjusted under 35 U.S.C. 154(b) by 283 days.

(21) Appl. No.: 10/280,704

(22) Filed: Oct. 25, 2002

(65) Prior Publication Data

US 2003/0055301 A1 Mar. 20, 2003

Related U.S. Application Data

(63) Continuation of application No. 10/181,185, filed as application No. PCT/EP01/13941 on Nov. 29, 2001, now abandoned.

(30) Foreign Application Priority Data

Nov. 29, 2000 (DE) .............................. 100 59 229
Feb. 13, 2001 (DE) .............................. 101 07 092

(51) Int. Cl.
*C07C 17/02* (2006.01)
(52) U.S. Cl. ................... 570/243; 570/244; 570/245
(58) Field of Classification Search ............... 570/243, 570/244, 245
See application file for complete search history.

(56) References Cited

U.S. PATENT DOCUMENTS 3,488,398 A * 1/1970 Harpring et al. .......... 570/243
3,996,300 A 12/1976 Ahlstrom, Jr. ............ 260/652

FOREIGN PATENT DOCUMENTS

| DE | 26 03 477 | 8/1977 |
| DE | 43 03 086 | 5/1998 |
| EP | 0 738 699 | 6/1999 |

* cited by examiner

*Primary Examiner*—Elvis Price
(74) *Attorney, Agent, or Firm*—Frommer Lawrence & Haug LLP; Ronald R. Santucci

(57) ABSTRACT

A process for the preparation of 1,2-dichloroethane that is very pure with respect to chloral or/and chloral hydrate and carbon dioxide is described herein. The process comprises oxychlorination of ethylene, using hydrogen chloride and an oxygen-containing gas, and alkali treatment of the 1,2-dichloroethane produced. In the process, the carbon dioxide present in the 1,2-dichloroethane-containing organic phase is, in accordance with the invention, substantially separated out from the 1,2-dichloroethane-containing organic phase before the alkali treatment.

19 Claims, 3 Drawing Sheets

PROCESS FOR PURIFYING 1,2-DICHLOROETHANE

This application is a continuation of U.S. Ser. No. 10/181,185 filed Jul. 10, 2002 now abandoned which is a national stage application of PCT/EP01/13941 filed Nov. 29, 2001 which was published in German. Both applications are incorporated by reference herein. PCT/EP01/13941 claims the benefit of priority under 35 U.S.C. §119 of German application DE 100 59 22.5 filed Nov. 29, 2000 and DE 101 07 092.6 filed Feb. 13, 2001.

BACKGROUND OF THE INVENTION

The invention relates to a process for the preparation of 1,2-dichloroethane that is very pure with respect to chloral or/and chloral hydrate and carbon dioxide, which process comprises oxychlorination of ethylene, using hydrogen chloride and an oxygen-containing gas such as air or oxygen, and alkali treatment of the dichloroethane, and also to 1,2-dichloroethane prepared in accordance with that process.

A known process for the preparation of 1,2-dichloroethane is the oxychlorination of ethylene using hydrogen chloride and oxygen, wherein chloral or/and chloral hydrate are formed as undesirable by-products. Also, the product of the process often comprises relatively large amounts of dissolved carbon dioxide formed as a by-product of the reaction of ethylene with oxygen.

The publication DE 1 518 931 describes an oxychlorination process for the preparation of 1,2-dichloroethane, wherein the undesirable chloral is removed by means of a condensing step. However, only 75 to 80% of the chloral can be separated out from the product by means of that process step. The remaining chloral is subsequently converted, by increasing the pH, into substances, for example chloroform, that can be more readily separated out by means of distillation.

Similarly, German Patent Specification 1 468 480 describes an oxychlorination process wherein the undesirable by-products chloral and/or chloral hydrate are converted into sodium formate and chloroform by means of alkali treatment and can therefore be readily separated out from the product of the process, 1,2-dichloroethane.

The disadvantage of both processes is that a large quantity of the alkali solution, especially aqueous alkali metal hydroxide solution, is consumed in neutralising the carbon dioxide and a corresponding amount of alkali metal carbonate or other salts is formed. Larger amounts of alkali solution therefore have to be used than would be necessary purely for converting the chloral and/or chloral hydrate. In addition, the salt charge formed in considerable measure as a result of the neutralisation has to removed from the production plant and disposed of.

The problem of the present invention accordingly was to provide, for the preparation of 1,2-dichloroethane, an oxychlorination process that avoids the disadvantages of the known processes. The problem of the present invention was especially to reduce, or to avoid altogether, the consumption of alkali solution, and the salt charge, during conversion of the undesirable by-products chloral and chloral hydrate and, at the same time, to prepare 1,2-dichloroethane that has only a low content of the said by-products, if any at all.

SUMMARY OF THE INVENTION

The problem is solved by a process for the preparation of 1,2-dichloroethane, which process comprises oxychlorination of ethylene, using hydrogen chloride and an oxygen-containing gas such as oxygen or air, and alkali treatment of the dichloroethane-containing reaction mixture and which is characterised in that carbon dioxide is especially removed from the 1,2-dichloroethane-containing organic phase before alkali treatment of the 1,2-dichloroethane is carried out.

It has been found to be especially advantageous for the carbon dioxide to be removed, to as great an extent as possible, from the reaction mixture before alkali treatment of the 1,2-dichloroethane because the formation of large salt charges can be avoided as a result. That spares the production plant and saves working time and costs, because it is no longer necessary, or only necessary to a reduced extent, to remove a salt charge from the production plant.

As a result of the process according to the invention, it is, in addition, advantageously possible to reduce the amount of alkali solutions to be used. The reduced lye requirement allows the production costs to be reduced. That is also advantageous and desirable from a health point of view as smaller volumes of lye have to be handled by the operating staff. In addition, therefore, less lye needs to be disposed of, which constitutes a considerable advantage both from a cost point of view and from an environmental point of view.

In accordance with the invention, pure or very pure EDC has, per kg of EDC, a 2-chloroethanol content of <100 mg, especially <50 mg, preferably <20 mg, more preferably <10 mg, even more preferably <5 mg, and very preferably <2 mg.

In accordance with the invention, very pure EDC has, per kg of EDC, a chloral content of <20 mg, preferably <10 mg, and very preferably <5 mg.

In accordance with the invention, very pure EDC has, per kg of EDC, an iron chloride content of <20 mg, preferably <10 mg, more preferably <5 mg, and very preferably <1 mg.

In accordance with one embodiment, the process of the invention preferably comprises the following process steps:

1. oxychlorination of ethylene using hydrogen chloride and oxygen,
2. quenching, washing and/or cooling and condensing of the reaction gases, that is to say of the products obtained from oxychlorination,
3. optionally, separation from the washing liquid,
4. distillation and condensing of 1,2-dichloroethane and, where applicable, water from the quench,
5. separation of the aqueous phase from the organic phase from step 4, optionally after transfer of the 1,2-dichloroethane-containing condensate into a separating vessel, optionally recycling of the aqueous phase to the quench, and optionally recycling of gases to the oxychlorination reaction,
6. removal of carbon dioxide from the 1,2-dichloroethane-containing phase (the reaction mixture),
7. alkali treatment of the 1,2-dichloroethane-containing phase, for example using an aqueous lye,
8. separation of the aqueous phase from the organic phase, optionally after transfer of the 1,2-dichloroethane-containing phase from step 7 into a separating vessel, optionally recycling of the aqueous phase to the quench,
9. obtaining 1,2-dichloroethane, and
10. optionally further working up or further processing steps.

The 1,2-dichloroethane obtained in that manner is very pure with respect to chloral/chloral hydrate.

The process conditions of individual steps, known per se, of the process according to the invention, especially the oxychlorination step and the alkali treatment step, can be carried out preferably in accordance with the process conditions described in the publication DE 1 518 931 and German Patent 1 468 480, the disclosures thereof being incorporated by way of reference in the present description.

A catalyst is preferably used for the oxychlorination step, with $CuCl_2$ or $FeCl_3$ catalysts having been found to be especially suitable for the purpose.

Before removal of the carbon dioxide, the reaction mixture is preferably blown into a washing-liquid-containing sump region, in the form of a bubble column, of a washing or quenching zone.

In accordance with a further embodiment of the process, the reaction mixture coming from the reaction zone, which reaction mixture may under certain circumstances include solids, with catalyst fragments under certain circumstances also being present in addition to the gaseous and/or liquid products of oxychlorination of the ethylene, is passed through a washing zone; the washing zone may comprise, for example, a column and a lower sump region arranged in the form of a bubble column. In the process, the reaction mixture preferably enters the lower portion of the bubble column, where it comes into intimate contact with the washing liquid present therein and, at the same time, is quantitatively freed of catalyst fragments. That process step can also be designated quenching.

The consumed washing liquid from the sump region of the washing zone is directed away, for example being neutralised and sent to waste water treatment.

The gaseous portion of the reaction mixture, which has been cooled and washed in the washing zone, is passed, by way of a gas line, into a condensing zone, in which there preferably prevail an elevated pressure and a low temperature.

The EDC-containing reaction mixture is substantially condensed therein, preferably under pressure, and is separated from the volatile by-products. The carbon dioxide is present in dissolved form in the condensate.

The carbon dioxide, present especially in the 1,2-dichloroethane-containing organic phase, may be separated out using any suitable procedure or apparatus. Separating the carbon dioxide out from the 1,2-dichloroethane-containing phase is preferably carried out by a method involving at least relieving the phase of pressure, for example in a vessel (desorption vessel). In that process, before the pressure is relieved, the phase has, for example, a pressure in the region of about 4 bar abs., whereas after the pressure is relieved it has, for example, a pressure in the region of about 1.1 bar abs. A vessel of that kind preferably has an outlet for drawing off the carbon dioxide (gaseous) and an outlet for the 1,2-dichloroethane-containing phase (liquid). That liquid phase can then be supplied to the further process steps by way of that outlet. A further process step is alkali treatment of the dichloroethane, which is already very pure with respect to $CO_2$, for the purpose of removing chloral and/or chloral hydrate.

In a further preferred embodiment, the carbon dioxide is separated out from the 1,2-dichloroethane phase in a column, by introduction of an inert gas. Any inert gas that is suitable in this process step may be used as the inert gas. The inert gas is preferably nitrogen. 1,2-Dichloroethane and inert gas are advantageously directed past one another in counterflow, as a result of which the mass transfer can be improved. A process course having concurrent flow is, however, also possible.

In yet another preferred embodiment, before the carbon dioxide is separated out, the 1,2-dichloroethane or the 1,2-dichloroethane-containing phases is/are heated, by the introduction of heat, it being possible to use the customary procedures and apparatus known to the person skilled in the art. Special preference is given to carrying out that process step using a heat exchanger.

The above-mentioned procedures relating to the removal of carbon dioxide may also be combined with one another as desired.

As a result of the separating out of carbon dioxide in accordance with the invention, it is possible to remove, completely or virtually completely, from the 1,2-dichloroethane-containing reaction mixture, especially from the organic phase, the carbon dioxide dissolved therein. After the separating out of carbon dioxide, the 1,2-dichloroethane-containing organic phase preferably has a carbon dioxide content of less than 0.3% (w/w), preferably less than 0.2% (w/w) and especially less than 0.06% (w/w).

The process according to the invention makes possible, by simple technical means and in economical manner, effective removal of the catalyst fragments and/or the carbon dioxide from the 1,2-dichloroethane-containing phase. The process according to the invention is first in resulting, in advantageous manner, in significant carbon dioxide separation, allowing a reduced use of base together with effective breakdown of chloral and/or chloral hydrate and accordingly resulting in a reduced salt charge.

In an especially preferred embodiment, the 1,2-dichloroethane-containing product from oxychlorination is quenched before the carbon dioxide is separated out.

In the context of the invention, quenching, for example in the form of cooling and condensing, means that unreacted starting materials, for example hydrogen chloride, are completely or at least substantially removed by means of suitable liquids, solutions, gases or gas mixtures. Quenching according to the invention has the advantage that, in the oxychlorination step, all, or the major portion, of unreacted starting materials are removed from the phase which is subjected to the further process steps.

The product from the oxychlorination process preferably contains, after quenching, less than 0.010% (w/w) hydrogen chloride, especially less than 0.005% (w/w) and most preferably less than 0.001% (w/w). As a result, undesirable reactions (corrosion) can advantageously be reduced or even avoided altogether.

Special preference is given to quenching by means of bringing into contact with an aqueous solution (washing solution), most preferably with water or an aqueous alkali solution.

The alkali treatment of the 1,2-dichloroethane-containing phase to be carried out after separating out the carbon dioxide may be accomplished using any suitable procedure and by means of customary apparatus. This process step is preferably carried out using an aqueous alkali solution. The aqueous alkali solution preferably has a pH of more than 8.5, especially more than 9.5.

Subsequently, further customary separation procedures known to the person skilled in the art, such as distillation, may be carried out in order to separate the chloral and/or chloral hydrate breakdown products and further constituents from the 1,2-dichloroethane.

The organic and aqueous waste products of the process are removed from the process circuit and are disposed of or recycled as necessary. The aqueous alkali solution obtained from the final process step is preferably recycled, especially together with further aqueous phases to which other process steps give rise. In the context of the invention, recycling is understood to mean that products of the process, intermediates or auxiliaries are returned to and used again in a process step.

In an especially preferred embodiment, the aqueous alkali solution, alone or together with the further aqueous phases, is recycled to the quench.

As a result of recycling the alkali solution to the quench, the pH of the quench is increased, as a result of which it is advantageously possible to improve the washing out of unreacted hydrogen chloride remaining from oxychlorination. Furthermore, additional neutralisation of the lye can, at least in some cases, be omitted.

The product of the process, 1,2-dichloroethane, obtained using the process according to the invention is substantially free of chloral and chloral hydrate. It preferably has a chloral or/and chloral hydrate content of less than 0.02% (w/w), preferably less than 0.005% (w/w) and especially less than 0.002% (w/w).

A further aspect of the invention relates to 1,2-dichloroethane that is very pure with respect to chloral and/or chloral hydrate and obtainable using a process as described above.

1,2-Dichloroethane according to the invention may advantageously be used in applications where chloral or chloral hydrate would have an adverse effect.

Further advantages and developments of the invention are shown by the patent claims, the drawings and the following description in which exemplary embodiments of the invention are described in detail with reference to the drawings.

DETAILED DESCRIPTION OF THE PREFERRED EMBODIMENT

Figure 1:
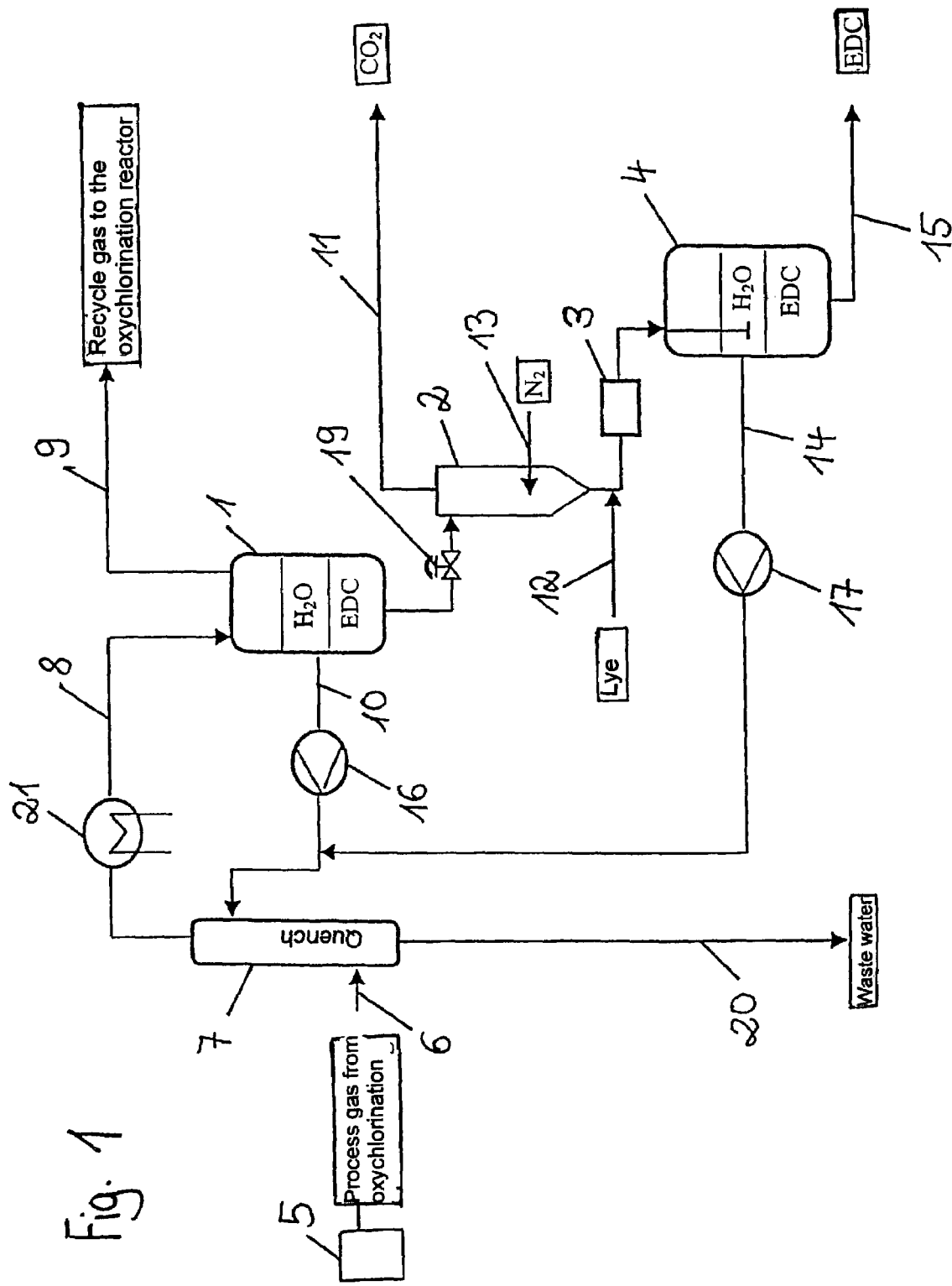
FIG. 1 showing a flow diagram of a process of the invention according to a first preferred embodiment.

FIG. 1 shows a flow diagram of a process according to the invention, wherein EDC denotes the 1,2-dichloroethane being produced and 5 denotes an oxychlorination step. The oxychlorination is carried out in known manner under customary conditions known to the person skilled in the art. The process gas of the oxychlorination step 5 is transferred to a quenching step 7 by way of a line 6. The reaction mixture obtained therefrom is transferred into a decanter 1 by way of a line 8 provided with a heat exchanger 21, whereas the waste water is directed away from the quenching step 7 by way of a waste water line 20. Recycle gases are recycled from the decanter 1, by way of a line 9, to the oxychlorination step 5.

The aqueous phase is separated off in the decanter 1 and it is recycled to the quenching step 7 by way of a line 10 by means of a pump 16. The 1,2-dichloroethane(EDC)-containing organic phase from the decanter 1 is relieved of pressure in a vessel 2 by way of a control valve 19, the carbon dioxide given off being removed by way of a carbon dioxide take-off line 11. In accordance with the preferred embodiment shown, an inert gas, in this instance nitrogen, can, in addition, be fed in by way of an inert gas supply line 13.

Then, in an apparatus 3, the 1,2-dichloroethane-containing phase is treated by introduction of lye by way of an inlet line 12. In a further decanter 4, the aqueous alkaline phase is separated from the organic 1,2-dichloroethane-containing phase and recycled to the quenching step 7 by way of a line 14 by means of a pump 17. Finally, by that means, 1,2-dichlorothane that is very pure with respect to chloral or/and chloral hydrate is obtained from the end product take-off line 15.

Figure 2:
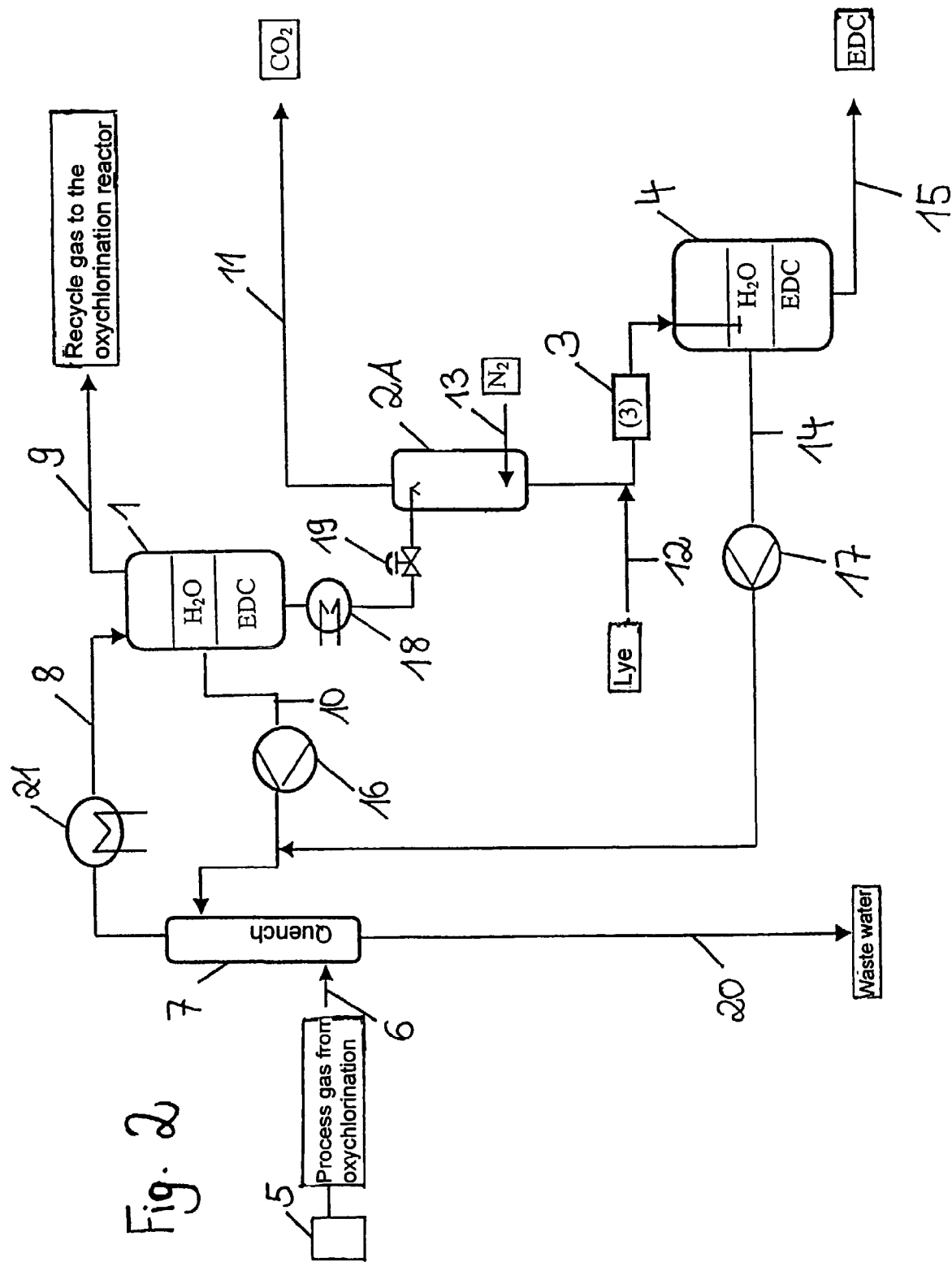
FIG. 2 showing a flow diagram of a further preferred embodiment of the process according to the invention.

FIG. 2 shows a flow diagram, corresponding to FIG. 1, in accordance with a further preferred embodiment of the invention. The difference from the process shown in FIG. 1 lies in the fact that carbon dioxide removal is carried out by means of a column 2A in conjunction with a heat exchanger 18, with inert gas, in this instance nitrogen, being introduced in counterflow; the heat exchanger 18 is situated upstream of the control valve 19. Otherwise, the course of the process corresponds to that shown in FIG. 1, for which reason corresponding parts and process steps are given reference symbols corresponding to FIG. 1.

Figure 3:
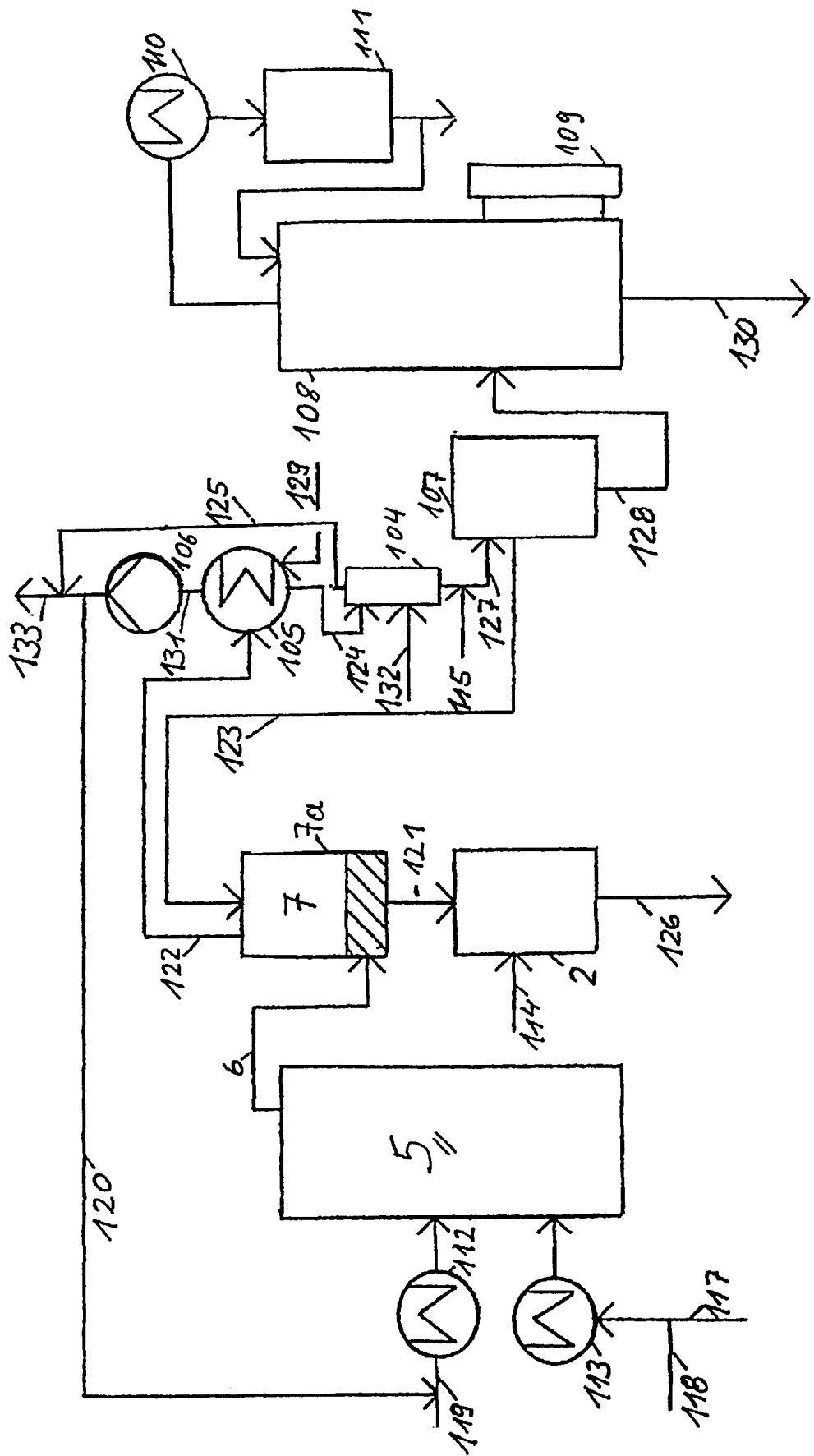
FIG. 3 showing a flow diagram of a further preferred embodiment of the process.

FIG. 3 shows an oxychlorination step 5, a washing or quenching zone 7, a vessel 2, a condensing step 105, a desorption zone 104, a separating zone 107 and a distillation zone 108 as central zones. In two heating zones 112 and 113, the process gases hydrogen chloride, oxygen, ethylene and recycle gas, that is to say gas obtained by recycling, are pre-heated and fed into the oxychlorination step 5.

6000 $Nm^3/h$ of hydrogen chloride and 1545 $Nm^3/h$ of oxygen are fed, through the hydrogen chloride line 117 and the oxygen line 118, respectively, into the second heating zone 113 and they are blown into the oxychlorination step 5 at a temperature of 140° C. 10000 $Nm^3/h$ of recycle gas and 3000 $Nm^3/h$ of ethylene are fed, through the recirculating line 120 and the ethylene line 119, respectively, into the first heating zone 112 and they are likewise blown into the oxychlorination step 5 at a temperature of 140° C.

The oxychlorination step 5 comprises a fluidised-bed reactor having a steam generator for dissipating the reaction heat; the reacted reaction gas flows out of the fluidised-bed reactor at a temperature of 210° C., through the reaction gas line 6 and into the lower region of the quenching or washing zone 7. The washing zone 7 comprises a column (dia.: 2.2 m) having 8 valve trays and having a sump region 7a arranged very especially in the form of a bubble column. The reaction gas enters the lower region of the bubble column, where it comes into intimate contact with the washing liquid and, at the same time, is quantitatively freed of catalyst fragments. In the washing zone 7, the reaction gas is cooled to a temperature of from 95° C. to 100° C. by the washing solution.

The washing liquid at the base of the bubble column runs off, through the run-off line 121, into the vessel 2 for the purpose of neutralisation by means of sodium hydroxide solution introduced by way of line 114 and is finally passed, by way of line 126, to the waste water plant for further treatment. The washed and cooled reaction gases are passed from the washing zone 7, through the gas line 122 and into the condensing zone 105.

Non-condensed recycle gas is passed, through the line 131, to the recirculating compressor 106 and is returned, by way of the line 120, to the oxychlorination step 5. A portion of the recycle gas is taken away by way of the waste gas line 133. By way of the condensate line 124, the EDC/water mixture, which is in liquid form under a pressure of about 4 bar and which contains dissolved carbon dioxide, at a temperature of 37° C. is relieved of pressure in the desorption zone 104, down to a pressure of about 1.6 bar, where it separates into carbon dioxide, which leaves at the top, and EDC/water mixture, which runs off at the base. It is also optionally possible for separation of water and the remaining reaction mixture to be carried out beforehand.

2 $Nm^3/h$ of nitrogen are fed into the condensing zone 105, by way of the line 129, for thorough mixing of the condensate, and 3 Nm³/h of nitrogen are fed into the pressure-relieving zone 104, at the base, by way of line 132, for stabilising the carbon dioxide flow, the addition of nitrogen also bringing about more effective or improved removal of the carbon dioxide.

While the carbon dioxide flowing out from the desorption zone 104 by way of line 125 is removed from the process in the form of waste gas (33 Nm³/h), the EDC/water mixture running off at the base is passed to the separating zone 107, by way of line 127, after thorough mixing with 25% sodium hydroxide solution from line 115, for the purpose of separating the two-phase mixture into an alkaline aqueous phase and an EDC phase.

Because both the aqueous phase and the EDC phase no longer contain dissolved carbon dioxide, after the introduction of sodium hydroxide solution the possibility of buffering in the system as a result of sodium hydrogen carbonate/sodium carbonate formation is ruled out and excellent, constant regulation of the specified pH in the range of from 10.5 to 13, preferably in the region of about 12, in the aqueous phase is ensured at all times for the purpose of chloral and 2-chloroethanol breakdown.

Maintenance of the pH is monitored by means of continuous measurement.

The aqueous phase obtained in that manner in the separating zone 107 can therefore be introduced into the quenching or washing zone 102 as washing liquid.

After an average dwell time, in the separating zone 107, in the region of preferably from 0.5 to 3 especially of about 1 hour, the upper, aqueous alkaline phase (having a pH adjusted to more than 9.5) is returned, by way of the line 123, to the washing/quenching zone 102 and the lower, 1,2-dichloroethane phase is passed, by way of line 128, into the distillation zone. The distillation zone 108 comprises a perforated-plate column (dia.: 2 m) having an evaporator 109, condenser 110 and separator 111.

While the low-boiling and aqueous portion is removed from the separator 111, the purified 1,2-dichloroethane is drawn off, by way of line 130, from the sump of the distillation zone 108 for the purpose of obtaining vinyl chloride by EDC cracking.

A certain portion both of the aqueous phase from line 123 and of the 1,2-dichloroethane phase from line 128 are returned to line 127 in order to achieve additional thorough mixing.

After start-up of the plant, the chloral, 2-chloroethanol and iron chloride contents in the purified 1,2-dichloroethane (EDC) were, at <2 mg of 2-chloroethanol/kg of EDC
<5 mg of chloral/kg of EDC
<1 mg of iron chloride/kg of EDC, below the limits of detection.

After a continuous production period of 6 weeks, the analytical impurity values did not change. Analysis of the 1,2-dichloroethane yielded the same results as had been obtained after start-up of the plant (see above).

For production of about 13500 t of EDC, a total of 327 t of 25% sodium hydroxide solution was added, corresponding to a specific consumption of 24.2 kg/t of EDC.

The process is distinguished by the fact that, in accordance with the invention, without a circulating procedure for the suspension, which may possibly contain solids, and irrespective of production changes and of the pH in the course of the washing and/or dwell zone, after separating out carbon dioxide in the desorption zone, the 1,2-dichloroethane/water mixture obtained from the condensing zone at a temperature of preferably from 25 to 45° as a result of its being relieved of pressure needs only to be subjected to alkali treatment with sodium hydroxide solution at an adjustable pH of preferably >8.5, especially >9.5, more especially in the range from 10.5 to 13, and for a dwell time of, for example, from 0.5 to 3 hours in the separating zone in order to obtain effective reduction of the chloral and 2-chloroethanol contents in the 1,2-dichloroethane and, therefore, to ensure the desired EDC quality for a lasting period. The iron chloride content in the product is below the limit of detection at all times.

In accordance with a preferred embodiment, a certain portion of the separated aqueous phase and/or organic phase can be returned to the line leading into the separating zone in order to achieve additional thorough mixing.

EXAMPLE 1

The course of the process in this instance is as shown in FIG. 1. The oxychlorination is carried out under customary process conditions, which will be known to the person skilled in the art and are therefore not explicitly mentioned here. The process gases from the oxychlorination step 5, essentially 1,2-dichloroethane, water and the undesirable by-products carbon dioxide, chloral and/or chloral hydrate and possibly further by-products, are quenched in a following process step (the quenching step 7) using an aqueous solution. In the process, traces of hydrogen chloride that have not been reacted during oxychlorination and, possibly, catalyst residues are washed out from the product mixture obtained from oxychlorination.

The 1,2-dichloroethane-containing phase, together with water, is then distilled off from the quenching step and condensed. For that purpose, the quench is distilled at a pressure of from 2 to 4 bar and at a temperature of from 90 to 110° C. in a suitable distillation apparatus, is condensed and is then transferred to a separating vessel, preferably a decanter 1. In the decanter 1, the aqueous phase is separated from the organic 1,2-dichloroethane-containing phase. The gaseous constituents therefrom can be recycled to the oxychlorination step 5. The aqueous phase is recycled to the quenching step 7 and the organic phase is relieved of pressure in a vessel 2, the carbon dioxide being substantially evolved from the 1,2-dichloroethane and drawn off through an outlet from the vessel. The carbon dioxide content in the 1,2-dichloroethane phase obtained is from 0.2% to 0.3% (w/w) carbon dioxide, based on the 1,2-dichloroethane-containing phase.

In the process step that follows, the 1,2-dichloroethane-containing, organic phase is transferred to an apparatus 3 located downstream and alkali treatment is carried out. For that purpose, a lye, preferably an NaOH solution having a concentration of <10% (w/w) is introduced into the apparatus 3, as a result of which the chloral and/or chloral hydrate is broken down.

The mixture is passed into a further decanter 4, in which the 1,2-dichloroethane and the alkaline aqueous phase are separated from one another. The alkaline aqueous phase is recycled to the quenching step 7, and 1,2-dichloroethane that is very pure with respect to chloral/chloral hydrate, having a chloral or/and chloral hydrate content of less than 0.002% to 0.005% (w/w) based on the 1,2-dichloroethane-containing phase, is obtained.

EXAMPLE 2

The course of the process is as shown in FIG. 2. The process steps and the course of the process therein also correspond to those of FIG. 1, with the difference that, for separating out the carbon dioxide from the 1,2-dichloroethane-containing phase, that phase is passed from the first separating vessel, a decanter 1, into a column 2A in which the carbon dioxide is separated off by means of the introduction of nitrogen by way of an inert gas supply inlet 13. After that process step, the 1,2-dichloroethane-containing phase has a carbon dioxide content of from 0.05% to 0.1% (w/w).

EXAMPLE 3

The process steps and the course of the process again essentially correspond to those of FIG. 1, with the difference that, for separating out the carbon dioxide from the 1,2-dichloroethane-containing phase, that phase from the first separating vessel, a decanter 1, is subjected to indirect introduction of heat by means of a heat exchanger, with nitrogen additionally being introduced into the column 2A. After that process step, the 1,2-dichloroethane-containing phase has a carbon dioxide content of from <0.05% to 0.06% (w/w).

The invention claimed is:

1. The process for the preparation of 1,2-dichloroethane comprising, oxychlorinating ethylene using hydrogen chloride and an oxygen-containing gas to form a 1,2-dichloroethane-containing reaction mixture, obtaining an organic phase including 1,2-dichloroethane from the 1,2-dichloroethane containing reaction mixture, and separating carbon dioxide from the organic phase by conveying the organic phase and an inert gas to a vessel prior to treating the organic phase with alkali.

2. The process according to claim 1 comprising separating the carbon dioxide by relieving the organic phase of pressure.

3. The process according to claim 1 wherein the inert gas is nitrogen.

4. The process according to claim 1 comprising separating the carbon dioxide from the organic phase by indirect introduction of heat with a heat exchanger.

5. The process according to claim 1 wherein after separation of carbon dioxide the organic phase has a carbon dioxide content of less than 0.3% (w/w).

6. The process according to claim 1 comprising at least one selected from the group consisting of quenching the 1,2-dichloroethane-containing reaction mixture, cooling the 1,2-dichloroethane reaction mixture and liquefying the 1,2-dichloroethane containing reaction mixture prior to separating the carbon dioxide.

7. The process according to claim 6 comprising quenching the 1,2-dichloroethane-containing reaction mixture by introducing the mixture into a sump region of a washing zone wherein the sump region is in the form of a bubble column and comprises a washing liquid.

8. The process according to any one of claim 6 or 7 comprising quenching by contacting the reaction mixture with a washing liquid that is an aqueous solution.

9. The process according to claim 1 further comprising treating the organic phase with an aqueous alkali solution after separating carbon dioxide.

10. The process according to claim 9 comprising separating the organic phase from the aqueous alkali solution after treatment with the aqueous alkali solution and wherein before the treatment, the aqueous alkali solution has a pH greater than 8.5.

11. The process according to claim 10 further comprising recycling the aqueous alkali solution.

12. The process according to claim 10 wherein the aqueous alkali solution is recycled to the quench.

13. The process according to any one of claim 10, 11, or 12 wherein after separation of the aqueous alkali phase from the organic phase, the aqueous alkali phase has a pH in the range of from 10.5 to 13.

14. The process according to claim 1 wherein the organic phase has less than 0.02% (w/w) of one selected from the group consisting of chloral, chloral hydrate and combinations thereof.

15. The process according to claim 1 comprising separating carbon dioxide wherein the organic phase has a carbon dioxide content of less than 0.1% (w/w).

16. The process according to any one of claim 10, 11 or 12 wherein after separation of the aqueous alkali phase from the organic phase, the aqueous alkali phase has a pH in the range of from 10.5 to 13.

17. The process according to any one of claim 6 or claim 7 comprising quenching by contacting the reaction mixture with water.

18. The process according to claim 1 wherein the organic phase has less than 0.005% (w/w) of one selected from the group consisting of chloral, chloral hydrate and combinations thereof.

19. The process according to claim 1 wherein the organic phase has less than 0.002% (w/w) of one selected from the group consisting of chloral, chloral hydrate and combinations thereof.

\* \* \* \* \*